US 8,523,925 B2

(12) United States Patent
Gourgouliatos et al.

(10) Patent No.: US 8,523,925 B2
(45) Date of Patent: *Sep. 3, 2013

(54) FIBER OPTIC PHOTOTHERAPY DEVICE

(75) Inventors: Zafirios Gourgouliatos, Los Angeles, CA (US); David Chang, Encino, CA (US)

(73) Assignee: Lerner Medical Devices, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/014,442

(22) Filed: Jan. 15, 2008

(65) Prior Publication Data
US 2008/0172113 A1    Jul. 17, 2008

Related U.S. Application Data

(60) Provisional application No. 60/880,813, filed on Jan. 17, 2007, provisional application No. 60/880,812, filed on Jan. 17, 2007, provisional application No. 60/880,887, filed on Jan. 17, 2007, provisional application No. 60/880,883, filed on Jan. 17, 2007.

(51) Int. Cl.
*A61B 18/18* (2006.01)
(52) U.S. Cl.
USPC .................................. 607/89; 607/88; 607/90
(58) Field of Classification Search
USPC .................. 607/88, 94, 74; 606/9, 16, 13
See application file for complete search history.

(56) References Cited

U.S. PATENT DOCUMENTS

| 2,397,757 | A | * | 4/1946 | Schwedersky | 607/79 |
|---|---|---|---|---|---|
| 3,261,978 | A | * | 7/1966 | Brenman | 15/105 |
| 3,590,232 | A | * | 6/1971 | Sadowski | 362/573 |
| 4,423,431 | A | | 12/1983 | Sasaki | |
| 4,520,816 | A | | 6/1985 | Schacher et al. | |
| 4,558,700 | A | | 12/1985 | Mutzhas | |
| 4,653,495 | A | * | 3/1987 | Nanaumi | 606/16 |
| 4,898,439 | A | * | 2/1990 | Mori | 385/31 |
| 5,300,097 | A | * | 4/1994 | Lerner et al. | 607/93 |
| 5,402,768 | A | * | 4/1995 | Adair | 600/106 |
| 6,053,180 | A | * | 4/2000 | Kwan | 132/232 |
| 6,074,411 | A | | 6/2000 | Lai et al. | |
| 6,254,625 | B1 | | 7/2001 | Rosenthal et al. | |
| 6,270,492 | B1 | | 8/2001 | Sinofsky | |
| 6,447,537 | B1 | | 9/2002 | Hartman | |

(Continued)

OTHER PUBLICATIONS

Taneja, A. et al., "Broad-band UVB fiber-optic comb for the treatment of scalp psoriasis: a pilot study", *International Journal of Dermatology*, vol. 43, pp. 462-467, 2004.

(Continued)

*Primary Examiner* — Bill Thomson
*Assistant Examiner* — Jeffrey Lipitz
(74) *Attorney, Agent, or Firm* — Lathrop & Gage LLP

(57) ABSTRACT

A phototherapy apparatus for the treatment of skin disease is disclosed including: an at least partially hollow body element; a plurality of light emitting elements enclosed within the body element; and a plurality of elongated light transmitting elements, each of the light transmitting elements having a proximal end detachably affixed to the body element in proximity to one or more of the light emitting elements, and extending to an end distal the body element. For each of the elongated light transmitting elements, at least a portion of light incident from the light emitting elements onto the proximal end is directed through the light transmitting element and emitted from the distal end.

32 Claims, 9 Drawing Sheets

(56) References Cited

U.S. PATENT DOCUMENTS

| | | | |
|---|---|---|---|
| 6,494,899 B1 | 12/2002 | Griffin et al. | |
| 7,194,316 B2* | 3/2007 | Bousfield et al. | 607/150 |
| 2001/0025190 A1* | 9/2001 | Weber et al. | 607/89 |
| 2002/0038485 A1* | 4/2002 | Nakagawa et al. | 15/28 |
| 2002/0128696 A1* | 9/2002 | Pearl et al. | 607/89 |
| 2002/0133144 A1 | 9/2002 | Chan et al. | |
| 2002/0156402 A1* | 10/2002 | Woog et al. | 601/46 |
| 2003/0057385 A1 | 3/2003 | Magne et al. | |
| 2003/0076281 A1 | 4/2003 | Morgan et al. | |
| 2003/0093915 A1* | 5/2003 | Pearl et al. | 34/96 |
| 2003/0187486 A1* | 10/2003 | Savage et al. | 607/89 |
| 2003/0233138 A1 | 12/2003 | Spooner | |
| 2005/0135102 A1 | 6/2005 | Gardiner et al. | |
| 2005/0143793 A1 | 6/2005 | Korman et al. | |
| 2005/0154382 A1 | 7/2005 | Altshuler et al. | |
| 2005/0251242 A1* | 11/2005 | Bousfield et al. | 607/150 |
| 2005/0267452 A1 | 12/2005 | Farr et al. | |
| 2006/0178712 A1* | 8/2006 | Carullo et al. | 607/89 |
| 2006/0201150 A1 | 9/2006 | Ferren et al. | |
| 2006/0206173 A1* | 9/2006 | Gertner et al. | 607/88 |
| 2006/0276862 A1 | 12/2006 | Irwin | |
| 2007/0179574 A1* | 8/2007 | Elliott | 607/94 |
| 2007/0208398 A1* | 9/2007 | Weber | 607/89 |
| 2008/0021528 A1* | 1/2008 | Carullo et al. | 607/89 |
| 2008/0131834 A1* | 6/2008 | Shepherd et al. | 433/29 |

OTHER PUBLICATIONS

PCT International Search Report (PCT/US08/00495); Date of mailing Jun. 18, 2008; 1 page.

PCT International Search Report (PCT/US08/00499); Date of mailing Jul. 7, 2008; 1 page.

PCT International Search Report (PCT/US08/00545); Date of mailing Jul. 11, 2008; 1 page.

* cited by examiner

| TYPE | TYPICAL UVB MED OF UNEXPOSED SKIN (mJ/cm$^2$) | RECOMMENDED START DOSE @ 2 MEDs (mJ/cm$^2$) | RECOMMENDED END DOSE* (mJ/cm$^2$) |
|---|---|---|---|
| I | 45 | 90 | 240–360 |
| II | 75 | 150 | 600–750 |
| III | 90 | 180 | 720–950 |
| IV | 120 | 240 | 900–1,100 |
| V | 150 | 300 | 1,000–1,200 |
| VI | 240 | 480 | 1,200–1,400 |

*DEPENDING ON PATIENT TOLERANCE.

TREATMENT DOSES FOR WAVELENGTH OPTIMIZED UV-B

*FIG. 6*

FIBER OPTIC PHOTOTHERAPY DEVICE

CROSS REFERENCE TO RELATED APPLICATIONS

The present application claims priority from U.S. Provision Application Ser. No. 60/880,883, U.S. Provisional Application Ser. No. 60/880,812, U.S. Provisional Application Ser. No. 60/880,813, U.S. Provisional Application Ser. No. 60/880,887, each filed Jan. 17, 2007, and each of which is incorporated by reference herein in its entirety.

BACKGROUND

This disclosure relates to treatments for inflammatory diseases of the skin, and more specifically to methods for devices and treating ultraviolet light-sensitive dermatoses.

Inflammatory diseases of the skin affect a large portion of the population resulting in significant morbidity. Psoriasis, for example, affects at least 1% of the population. This disease involves an abnormally fast rate of cell proliferation in the basal layer of the epidermis giving rise to red, scaly plaques and bleeding when traumatized (the "Auspitz sign"). Past methods of treatment of skin psoriasis include the application of tars, salicylic acid, steroids, ultraviolet light (phototherapy), and a combination of ultraviolet light, used in conjunction with photoactive compounds (photochemotherapy).

Photochemotherapy involves treatment with ultraviolet radiation of an affected area in combination with a topically or systemically applied medicament that sensitizes the skin to ultraviolet radiation (e.g., psoralen). Typically ultraviolet-A (UV-A) light (so-called long wave UV light) having wavelengths from 310 to 440 nm is used for this purpose. Unfortunately, successful treatment requires that UV radiation must be applied until an erythema (sunburn) is created. In some cases, the eyes of patients systemic undergoing psoralen and topical UV treatment may be sensitized to sunlight for several hours after treatment. In addition, some patients find the medicament difficult to tolerate. Furthermore, this therapy requires 20-25 radiation sessions which result in darkening of the pigmentation of the skin. In addition, treatment of scalp psoriasis in particular has been limited by two other problems. First, patients are reluctant to apply medications regularly which must remain on their scalps for hours at a time. Second, light from conventional treatment devices does not effectively penetrate hair covering the scalp.

Phototherapy involves simply UV irradiation of the affected area. For example, psoriasis has been treated with ultraviolet-B (UV-B) light having wavelengths from 290-320 nm. Other skin diseases which have been treated successfully with ultraviolet light include eczema, mycosis fungoides, and lichen planus. In addition, ultraviolet light may have a role in the treatment of seborrheic dermatitis.

Phototherapeutic methods have included the use of mercury vapor high pressure radiation devices and those UV sources having varying spectral distribution. For example, UV-B lamps such as devices which produce radiation from a metal halide or mercury vapor source and which filters the emitted UV light with colored glass have been used (see e.g., U.S. Pat. No. 4,558,700). These devices emit UV in the range of 270-365 nm (mostly 270-315 nm), and cause erythema. Devices which emit wavelengths of 320-330 nm and greater have also been used for so-called super-high-intensive phototherapy (SHIP).

A prior art device is adapted to deliver UV radiation to the scalp. That device is a hair brush for purportedly promoting the healthy flow of blood to the glands and roots of hair, and for promoting vitamin D production. The hair brush has an internal UV radiation source and UV radiation-transmitting bristles of a material other than a fiber optic material (Schwedersky, U.S. Pat. No. 2,397,757). Because the bristles of this device are rigid and pointed, its use on psoriasis-affected skin heightens the incidence of the Auspitz sign, and thus is contra-indicated for treatment of psoriasis.

Lerner, et al., U.S. Pat. No. 5,300,097, describes a light delivery apparatus which includes a body member and a plurality of optical fibers extending therefrom. The optical fibers are adapted to couple the light generated at the optical source from the proximal tips of the optical fibers, through the fibers, and to their distal tips. Each fiber has a proximal tip affixed to the body member and a distal tip at the end opposite the proximal tip. Also described are methods of treating inflammatory dermatoses using the light delivery apparatus. The method includes contacting a region of the body afflicted with a dermatosis with the distal tips of the device such that UV light emanating therefrom is incident on the contacted region. In some cases, the method includes the additional step of, prior to the contacting step, applying a medicant or lubricant to the region to be treated.

Therefore, a need exists for a simple device and method useful for treating affected areas of the skin, particularly those hair-covered regions such as the scalp.

SUMMARY

The present disclosure describes therapy devices for effective treatment of inflammatory dermatoses such as psoriasis. In various embodiments, these devices include an optical source including means for generating ultraviolet (UV) light (radiation) in a predetermined spectral range, and a light delivery apparatus.

In light of the above, it is an object of this disclosure to provide a therapeutic device for the delivery of UV irradiation directly to an area of the body afflicted with psoriasis or other related dermatoses.

Yet another object is to provide a method of treating psoriasis and related dermatoses which is easy to administer, rapid, and which minimizes unpleasant side effects such as erythema, pigmentation darkening, and the Auspitz sign.

An additional object of the disclosure is to provide a method of treating psoriasis which minimizes the therapeutic sessions required to result in relatively rapid healing.

These and other objects will be apparent from the drawing description, and claims that follow.

In one aspect, a phototherapy apparatus for the treatment of skin disease is disclosed including: an at least partially hollow body element; a plurality of light emitting elements enclosed within the body element; and a plurality of elongated light transmitting elements, each of the light transmitting elements having a proximal end detachably affixed to the body element in proximity to one or more of the light emitting elements, and extending to an end distal the body element. For each of the elongated light transmitting elements, at least a portion of light incident from the light emitting elements onto the proximal end is directed through the light transmitting element and emitted from the distal end.

In some embodiments, the plurality of light emitting elements include at least one from the group of: a light emitting diode, a quantum dot, a solid state laser.

In some embodiments, the plurality of light emitting elements have a spectral output within the range of 280 nm to 320 nm, within the range of 310 nm to 320 nm, or within the range of 320 nm to 380 nm.

In some embodiments, one or more of the elongated light transmitting elements includes an optical fiber.

In some embodiments, one or more of the elongated light transmitting elements includes a hollow tube, the interior surface of the tube having a reflective coating.

Some embodiments include a support element adapted to be detachably received by the body element and to support the elongated light transmitting elements. Each of the elongated light transmitting elements extends through the support element from a side of the support element proximal the body element to a side of the support element distal the body element. In some embodiments, the elongated light transmission elements and supporting element are autoclavable.

In some embodiments, the elongated light transmitting elements are arranged in a regular array. In some embodiments, the array is a two dimensional array. In some embodiments, the array is arranged to provide substantially uniform fluence of light emitted from the distal ends of the elongated light transmitting elements at an area of a treatment surface.

In some embodiments, the distal ends of the light transmitting elements are arranged in an array. In some embodiments, the array is a two dimensional array. In some embodiments, tips of the distal ends of the light transmitting elements are located at positions in space having a locus characterized by a curved surface or arc. In some embodiments, the curved surface or arc includes one of the group of: a circular arc, a parabolic arc, and ellipsoidal arc, a cylindrical segment, a spherical segment, a toroidal segment. In some embodiments, the curved surface or arc has an associated radius or radii of curvature within the range of about 2 inched to about 6 inches. In some embodiments, the locus is adapted to substantially conform to the shape of a human scalp In some embodiments, the array is arranged to provide substantially uniform fluence of light emitted from the distal ends of the light transmission elements at an area of a treatment surface.

In some embodiments, the distal end of one or more of the light transmitting elements includes a bulbous tip included of a light emitting spherical segment. In some embodiments, the spherical segment has a radius of curvature within the range of about 0.25 mm to about 3.0 mm In some embodiments, the distal end of one or more of the light transmitting elements includes a rounded tip. In some embodiments, the rounded tip has a radius of curvature within the range of about 0.25 mm to about 3.0 mm In some embodiments, the fiber includes a inner core surrounded by an outer cladding, the inner core having a radius within the range of about 0.1 mm to about 3 mm.

Some embodiments include a sensor adapted to sense the proximity or contact of the distal end of one or more of the elongated light transmitting elements to a treatment surface.

In some embodiments, at least one alignment element is adapted to receive the proximal end of one of the elongated light transmitting elements and to maintain the proximal end in a desired position relative to one or more of the light emitting elements.

In some embodiments, a proximal end of at least one of the elongated transmitting elements includes a retractable cover element, the retractable cover element adapted to cover at least a portion of the proximal end when the proximal end is detached from the body element and to retract from the proximal end when the proximal end is affixed to the body element in proximity to one or more of the light emitting elements.

In some embodiments, at least one of the light emitting elements includes a retractable cover element, the retractable cover element adapted to cover at least a portion of the least one light emitting when a proximal end of at least one light transmitting element is detached from the body element, and to retract from the at least one light emitting element when the proximal end is affixed to the body element in proximity to the at least one light emitting element.

Some embodiments include a control unit in communication with the light emitting elements configured to selectively adjust the duration or intensity of light transmitted from the light emitting elements to the light transmitting elements. In some embodiments, the control unit is in communication with a power supply, and is configured to control the power supplied to the light emitting elements to adjust the duration or intensity of light transmitted from the light emitting elements to the light transmitting elements. In some embodiments, the control unit includes a timer.

Some embodiments include a dosimetry sensor adapted to, during operation, provide information to the control unit indicative of a dose of treatment light directed from the light transmitting elements to a treatment surface. In some embodiments, the control unit is configured to selectively adjust the duration and intensity of light transmitted from the light emitting elements to the light transmitting elements based on the information.

Some embodiments include the power supply, where the power supply. The power supply may be enclosed within the body element.

In some embodiments, the body element is substantially opaque to light emitted by the light emitting elements.

In another aspect, a treatment system is disclosed including: a plurality of the phototherapy devices adapted to provide treatment light to a treatment area. Each device includes: an at least partially hollow body element; a plurality of light emitting elements enclosed within the body element; and a plurality of elongated light transmitting elements, each of the light transmitting elements having a proximal end detachably affixed to the body element in proximity to one or more of the light emitting elements, and extending to an end distal the body element; where, for each of the elongated light transmitting elements, at least a portion of light incident from the light emitting elements onto the proximal end is directed through the light transmitting element and emitted from the distal end. The system also includes a control unit adapted to selectively supply power to each of the plurality of the phototherapy devices.

In some embodiments, the control unit is capable of simultaneously supplying power to at least two of the plurality of phototherapy devices.

In some embodiments, the plurality of the phototherapy devices includes at least two phototherapy devices each adapted to provide treatment light at a different spectral range than the other.

In yet another aspect, a method of treating an area of skin affected by skin disease is disclosed including: providing treatment light to the affected area from a phototherapy device. The phototherapy device includes: an at least partially hollow body element;

a plurality of light emitting elements enclosed within the body element; and a plurality of elongated light transmitting elements, each of the light transmitting elements having a proximal end detachably affixed to the body element in proximity to one or more of the light emitting elements, and extending to an end distal the body element; where, for each of the elongated light transmitting elements, at least a portion of light incident from the light emitting elements on the proximal end is directed through the light transmitting element and emitted from the distal end.

In some embodiments, providing treatment light includes bringing the distal ends of the light transmitting elements into proximity or contact with the affected area.

In some embodiments, the providing treatment light includes, while maintaining distal ends of the light transmitting elements into proximity or contact with the affected area, moving the distal ends across the affected area to provide at least one minimal erythema dose of treatment light to the affected area.

In some embodiments, at least a portion of the affected area is a hair bearing region, and moving the distal ends across the affected area includes combing the distal ends through the hair.

It is to be understood that, as used herein, skin disease includes inflammatory skin disease such as psoriasis, vitiligo, pigmentation loss, and other disorders.

Various embodiments may include any of the above described features, alone or in any combination. These and other features will be more fully appreciated with reference to the following detailed description which is to be read in conjunction with the attached drawings.

DESCRIPTION OF THE DRAWINGS

FIG. 6 is an exemplary phototherapy dosage table;

Like reference numerals refer to like elements throughout the figures.

DESCRIPTION OF THE PREFERRED EMBODIMENT

Figure 1:
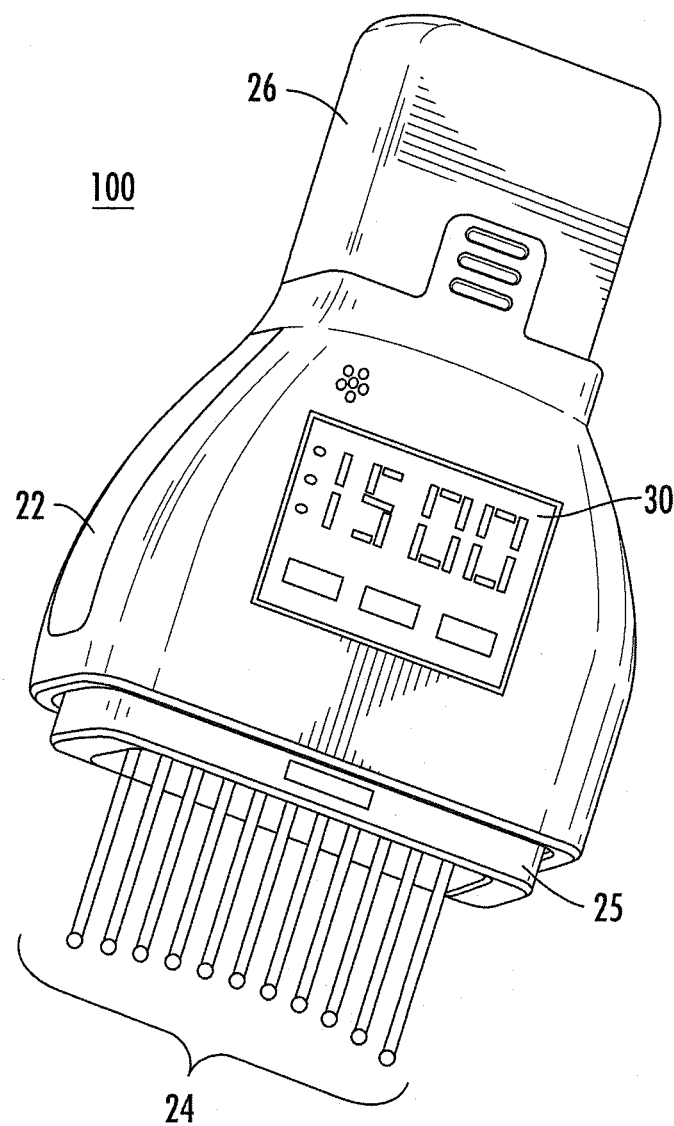
FIG. 1 is a perspective view showing an exemplary phototherapy device.

Therapeutic device 100 is shown in FIG. 1, and includes a light delivery apparatus including body member 22 and a plurality of light transporting elements, such as optical fibers 24 detachably extending therefrom. The light emitting elements are affixed on a support plate 25. The body member 22 encloses internal light emitting elements (shown in FIG. 2). It also encloses power, supplying element, auditory signal transducer and control network. On the surface of the body there is a status indicator and control buttons assembly 30. On the end opposing the light emitting elements there is detachable cup 26.

Figure 2:
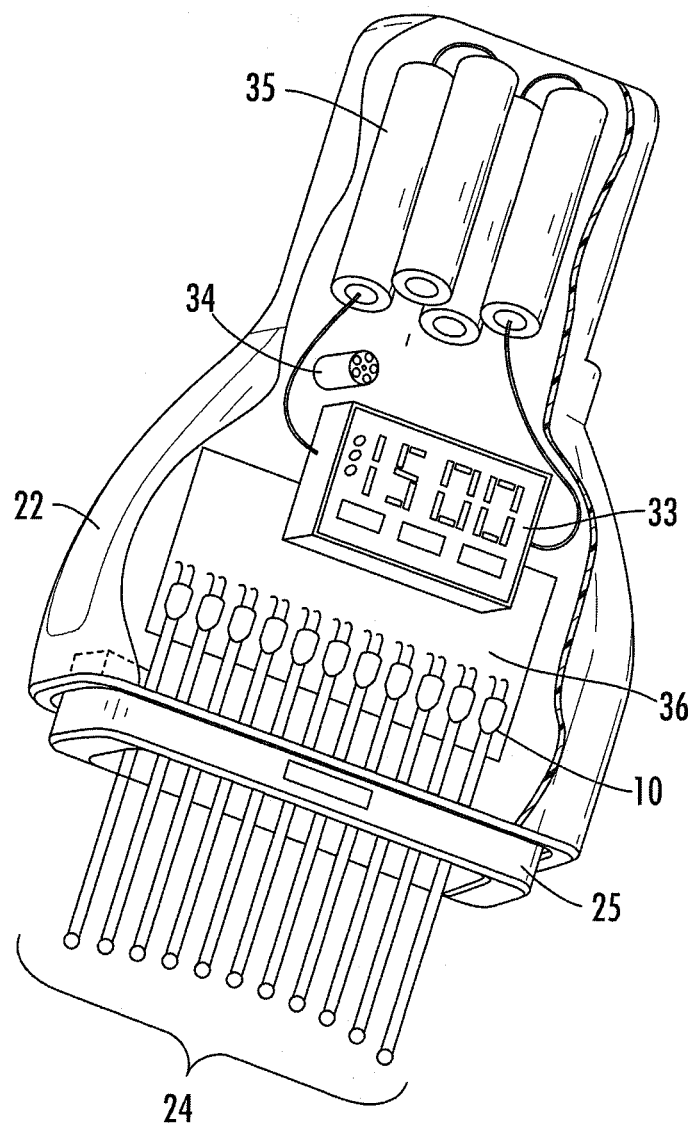
FIG. 2 is a view of the parts the embodiment of FIG. 1.

As shown in detail in FIG. 2, body member 22 is a substantially rectangular cross section body. That body is partially hollow and houses an array of light emitting elements 36. The optical fibers 24 extend from their proximal ends which are affixed in proximity to array light emitting elements 36, of which light emitting element 10 is a member. Preferably, body member 22 has substantially no UV-transferring abilities, and is formed of a molded resinous material, such as plastic, rubber, and the like.

Body member 22 includes on-board batteries 35 as a power source, control module with display and input elements 33, auditory signal transducer 34 for operator warnings.

Of course, in some embodiments power source and control module 30 may instead provide power via cable 32 through body member 22 to the control module 33 and optical source 36.

Figure 4A:
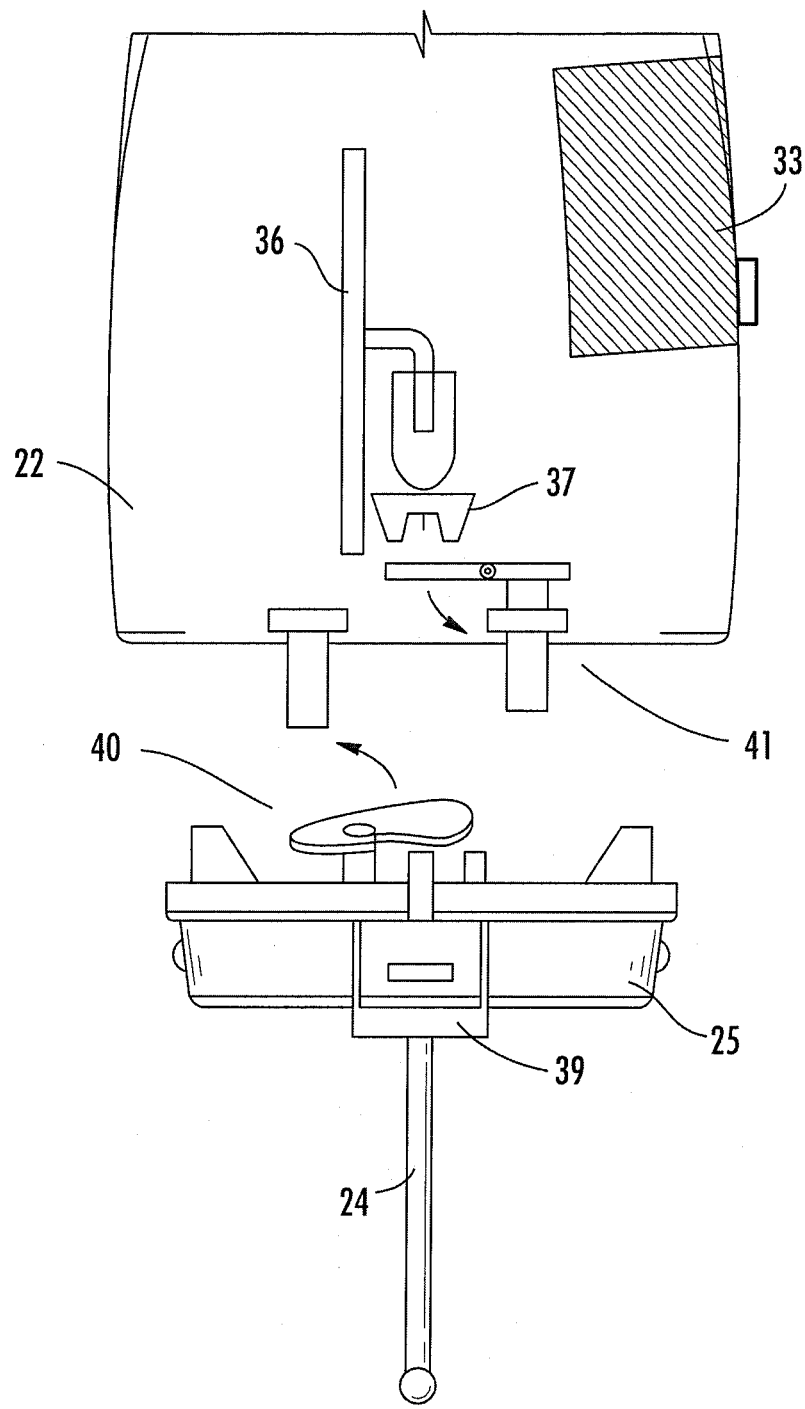
FIGS. 4a and 4b is a detailed view of the arrangement of light emitting elements, coupling element, retractable cover and contact transducer.
Figure 4B:
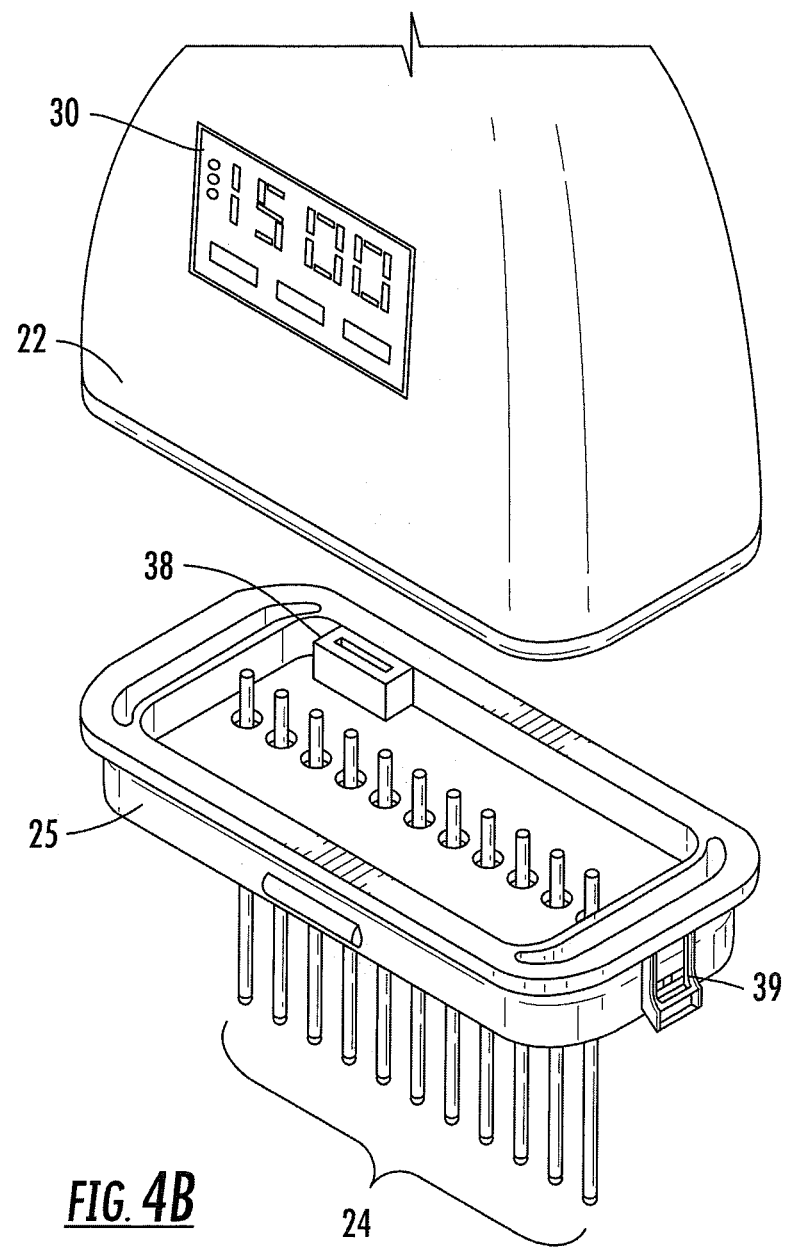

Light transmitting elements may be affixed on a support plate 25 that detachably attaches to body member 22 (FIG. 4a). Of course, light emitting elements 36 and light transmitting elements 24 preferably employ alignment element 37, to maximize optical power coupling. A detection element 38 (FIG. 4b) on the plate or between the body member 22 and plate 25 detects proximity or contact of fiber distal tips to the epidermis. For example, detection element 38 may be a pressure sensor which detects and increase in pressure between plate 25 and body member 22 which occurs when force is transferred from the tips contacting the epidermis through the fibers to support 25. Alternatively, pressure detection elements may measure force on one or more of the fibers directly. This detection element communicates with the control module, which can act to inhibit light emission when the fiber distal tips are not in proximity or contact with the skin. This increases safety, for example, by preventing the user from accidentally shining light from the fiber tips into his or her eyes, thereby causing vision damage.

Similarly, detection element 38 may detect the connection of support 25 with body member 22. The detection element would then communicate with the control module to inhibit light emission from light emitting elements 36. This again increases safety by preventing light from escaping from the opening created when support 25 is removed.

The detachable plate 25 may be secured to the body 22 with indentation mechanism 39 that allows easy retraction form the body so that a different plate with the light transmitting elements can be attached to the body at a time. This will enable the body to operate with plate and light transmitting element assemblies that are either single use or each assembly is designated for different patient.

Light emitting elements and light transmitting elements employ retractable covers 40 and 41 that retract when the plate is affixed to the body to allow optical coupling and reaffirm when separated to protect light emitting elements and light transmitting elements.

Optical source 10 depicted in FIG. 2 can be any of the light emitting diodes (LED), quantum dots or solid state lasers.

Figures 3A, 3B:
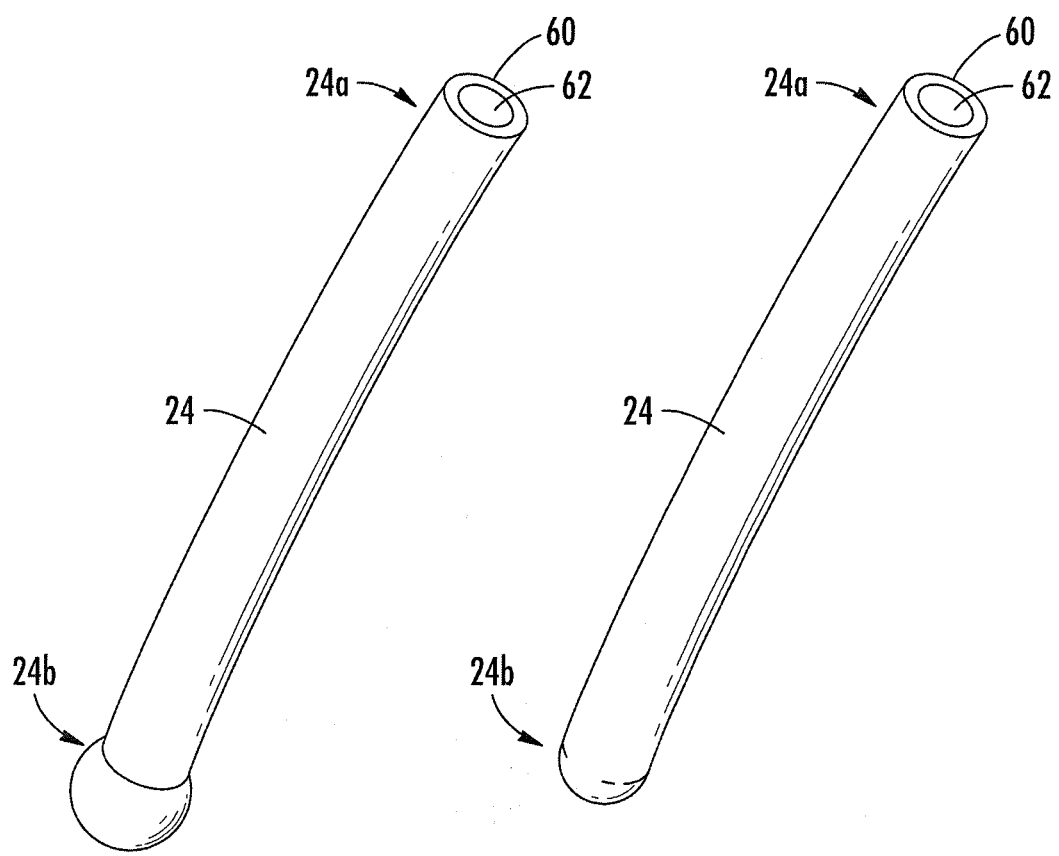
FIGS. 3A and 3B show detailed perspective views of exemplary fibers of the device of FIG. 1.

Two alternative forms for the individual optical fibers 24 are shown in FIGS. 3A and 3B. Each fiber is adapted for fixture to support element 25 at its proximal end 24a. Proximal tips 24a of fibers 24 may be embedded as individual elements within support element 25. Each of fibers 24 includes a central core 60 having a diameter in the range of 0.1-3 mm, and an outer cladding 62. Distal tips 24b of fibers 24 are spherical segments. In the embodiment of FIG. 3A, those tips have a UV light transmitting spherical element 64, while in the embodiment of FIG. 3B, the ends of the fiber 24 is rounded. The distal tip have a radius of curvature in the range of about 0.25-3.0 mm, to ensure that minimal damage is done to the skin during use. They should be smooth and small enough to easily be moved through the hair in brush-like fashion. Central core 60 is composed of a material which is capable of transmitting UV irradiation, such as fused silica, solarization resistant fused silica, plastic, or glass. Outer cladding 22 is preferably formed from similar materials, including polymers, but of lower refractive index. Of course, in some alternative embodiment, the light transmitting element can be a hollow tube with internal diameter of 0.1-3 mm with polished, UV reflecting internal surface. Fibers 24 are hardy and ideally are autoclavable or able to be gas sterilized.

Fibers 24 may be arranged in linear or rectangular arrays, or positioned in particular patterns as dictated by the geometry of the region-to-be-treated and which facilitates uniform dosimetry during use. Movement of the fiber arrays allows a selected area to be treated completely. The length of fibers 24 may also be variable for the same reason. For example the distal ends of the light transmitting elements may be located at positions in space having a locus characterized by a curved surface or arc. In some embodiments, the curved surface or arc may include a circular arc, a parabolic arc, and ellipsoidal arc, a cylindrical segment, a spherical segment, a toroidal segment. The curved surface or arc has an associated radius or radii of curvature within the range of about 2 inched to about 6 inches. The locus may be adapted to substantially conform to the shape of a human scalp The therapeutic device described above can be easily used to treat inflammatory dermatoses affecting body regions covered by hair, such as the scalp. Fibers 24 can be positioned so that the distal tips 24b are pressed gently through such encumbrances to contact the scalp during use. The blunting or rounding of distal tips 64 help to prevent development of the Auspitz sign during normal use.

Figure 8:
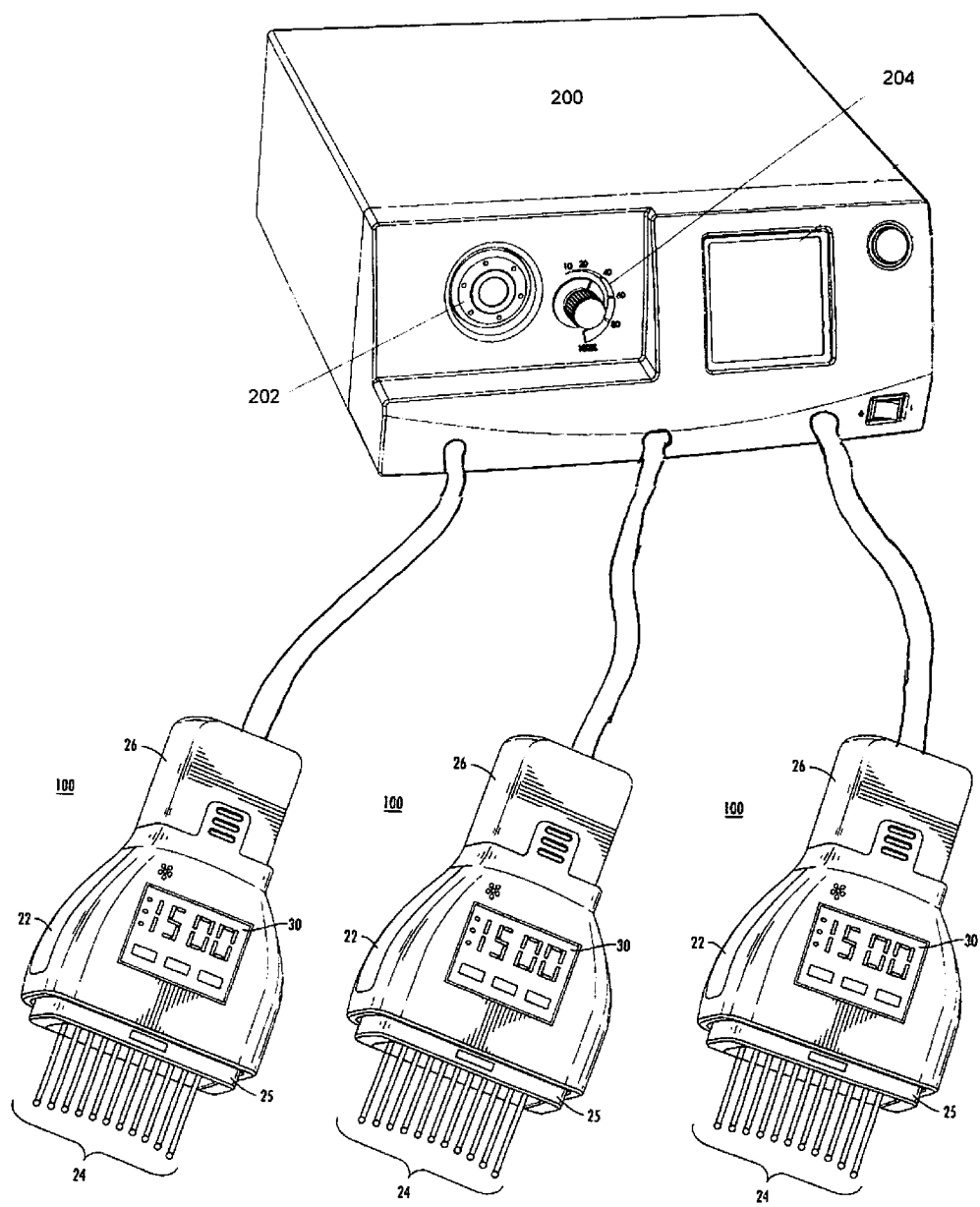
FIG. 8 shows an exemplary embodiment of the invention having three phototherapy devices coupled to a control device.

In a treatment system, a control device/unit 200 can include the power supply unit with operator controls 202, 204 for selectively adjusting the duration and intensity of the UV radiation that is transmitted to the fibers 24 of each body member 22 of a device 100. The body member 22 can have alternative configurations so that the handle is on the side. As shown in FIG. 8, the control device/unit 200 can power more than one body member 22 for simultaneous use. Alternatively, each device 100 can emit treatment light at different spectral ranges from each of the individual body members 22.

The advantage of this device is that areas of the skin, such as the scalp, which were previously difficult and time consuming to treat, may now be easily treated. Also, localized areas of the skin may be treated without exposing the entire body to 8-MOP and/or to UV light.

In a preferred embodiment, the light emitting elements can emit light in the spectral range of 280-320 mm, preferably in the 310-320 nm for dermatoses that respond to UV-B light. Alternatively they can emit light in the 320-380 nm for dermatoses that respond to UV-B light, in other spectral bands of visible or infrared light for dermatoses or skin conditions that respond to specific wavelengths.

Preferred embodiments of the method of treating an inflammatory dermatosis using the aforementioned device are as follows.

For UV-B phototherapeutic treatment, simple application while gently combing through the hair for prescribed times necessary is acceptable, beginning with approximately one minimum erythema dose (MED) during the first treatment. Subsequent treatment times would increase if needed and as tolerated by the skin.

In practice, the delivered exposure dose (fluence) needs to be controlled to within about 40% absolute. Both short-term and long-term output stability, including solarization of spectral filters or windows, are considerations affecting dosimetry. If the source output is stable (e.g., less than 10% variation of UV irradiance) after a short warm-up period, over the duration of one treatment (typically tens of minutes), then a timer type of device to control delivered dose based on a measured irradiance is appropriate. If the output is unstable, an integrating dosimeter is required. The ideal system would be stable, might require the user to point the output onto a detector which measured irradiance appropriately, then enter the desired dose in $J/cm^2$ or other suitable units.

Natural skin oils, water, or light lubricants applied to the scalp beneficially modify the optics of psoriatic skin, further reduce trauma, and provide good index matching to silica fibers. The delivery of UV radiation into the skin via direct contact with a UV-transmitting optical fiber is more efficient than through air, due to refractive index mismatching between the skin ($n_d$=1.55) and air ($n_d$=1.00). By directly contacting the scalp with the preferred fiber optic core material, fused silica ($n_d$=1.46), specular reflection at the scalp surface is greatly reduced, especially when a lubricant or topical application of psoralen-containing solution is present. The amount of such specular reflection varies mainly with the square of the difference in psoriasis, there is poor formation of the outermost skin layer. Thus, coupling of UV light into the psoriasis skin is much more efficient with direct contact between the fiber optic source and skin, in the presence of a lubricant or topical solution.

Of course, other areas of the skin such as the nails could also be treated as described above.

CLINICAL EXAMPLES

The following describes the clinical use of a phototherapy device and methods of the type described above.

Figure 5:
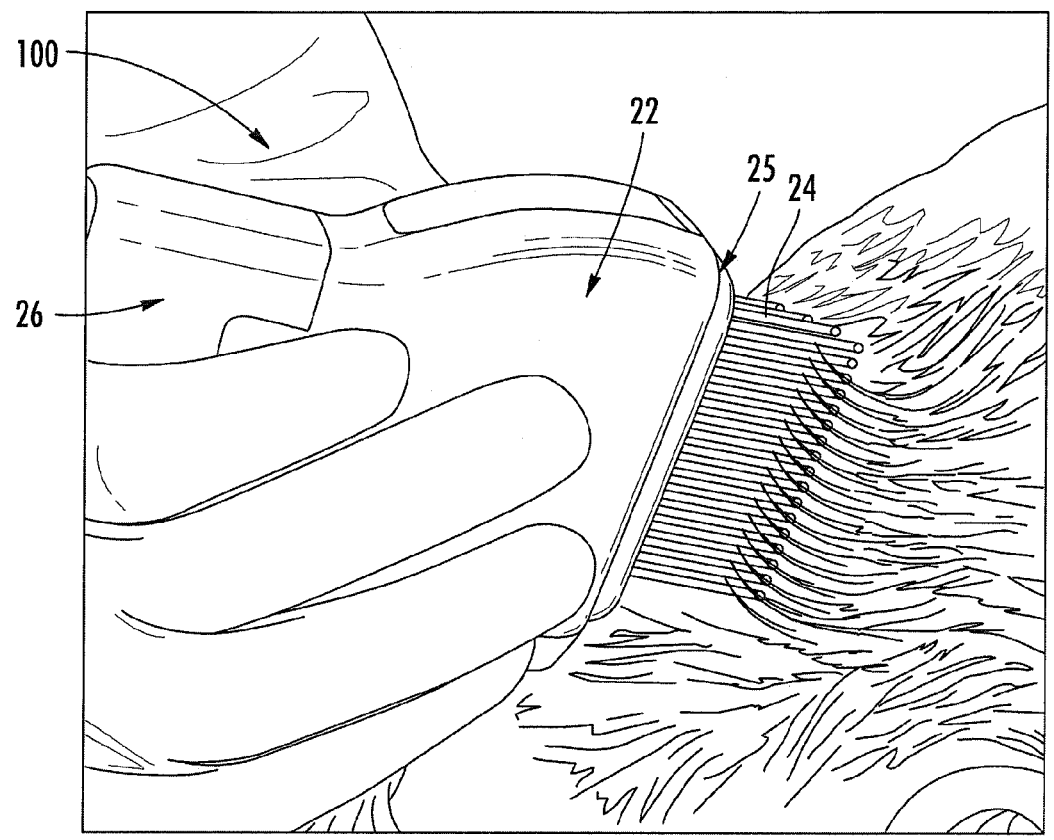
FIG. 5 is a photograph of an exemplary phototherapy device in clinical use.

As shown in FIG. 5, the scalps of patients were treated with a fiberoptic brush phototherapy device 100 of the type described above. The bristles of the brush consisted of optical fibers 24 allowing combing to deliver light to the scalp. Without this delivery system hair would absorb light and prevent it from reaching the scalp. Mineral oil was applied as in the spot treatment. Exposure levels were similar to those noted above for non-scalp areas. The phototherapy device 100 produced 25 mW/cm2 at full output. The output level was varied to allow delivery of the appropriate dose. FIG. 6 shows a table of exemplary dosages for various classifications of skin type, as will be understood by those skilled in the art.

Figure 7:
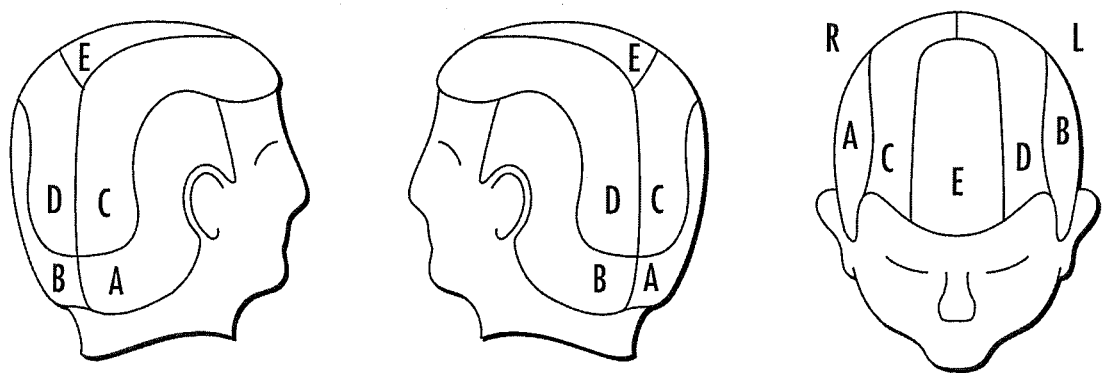
FIG. 7 is an illustration showing the division of a human scalp into treatment areas.

As illustrated in FIG. 7, in patients with a full head of hair, the scalp was divided into five zones A, B, C, D, E. The zones were treated for time intervals that ranged from thirty seconds to four minutes. The treatment time for the entire scalp reached a maximum of fifteen minutes. For patients with skin Type II, as is know in the art, the initial dose was set at 2 MEDs and was increased by 15-20% on each treatment. The hair was parted at that area with the fingers. If the patient complained of burning sensation discomfort, the dose was not increased or the increase was moderated. The same applied on the few occasions the patient skipped a treatment.

Patients were treated twice a week for a total of twelve treatments. If spots cleared earlier, treatment was discontinued when there was no visible lesion or hyperpigmentation on the skin. Considering that some patients missed a treatment now and then, the total time was 7-8 weeks. For the scalp preservation treatment was given once per week or every other week.

Patient 1 was a Caucasian male, 35 years old with skin type: III. His medical history included: stable psoriatic plaques on the scalp last 5 years. Previous treatment involved emollients, steroid creams, peanut oil, and tar shampoos. No topical (or systemic) treatments were given for 4 weeks prior to targeted UVB therapy. The patient's treatment occurred two times a week for a total of twelve treatments. The scalp was treated with a fiberoptic brush phototherapy device of the type described above. For the scalp, the initial dose was 180 $mJ/cm^2$ and was increased by 15-20% on each treatment until it reached 950 $mJ/cm^2$. On the scalp, clearance was achieved with 8 treatments. Preservation treatment was continued once a week for 6 weeks. The patient was clear on the last examination, 4 weeks after the last treatment.

Patient 2 was a Caucasian male, 27 years old with skin type II. His medical history included: stable psoriatic plaques on head, arms, legs and body. Previous treatment involved emollients, tar shampoos, occasional steroid creams, and various herbal therapies. No topical or systemic treatments were provided for 4 weeks prior to targeted UVB therapy. The scalp was treated with a fiberoptic brush phototherapy device of the type described above. Patient 2's treatment was similar to patient 1 but cleared faster and treatment was discontinued. The patient cleared after 6 weeks of treatment (ten treatments) and treatment was interrupted once he was clear. Preservation treatment was not given. The patient was clear on the last examination, 8 weeks after treatment.

Patient 3 was a Caucasian male, 52 years old with skin type II. His medical history included: stable psoriatic plaques on the scalp. Previous treatment involved emollients, steroid creams, and tar shampoos. No topical (or systemic) treatments were given for 4 weeks prior to targeted UVB therapy. Treatment was provided two times a week for a total of twelve treatments. The scalp was treated with a fiberoptic brush phototherapy device of the type described above. For the scalp, the initial dose was 150 mJ/cm$^2$ (about 2 MEDS) and was increased by 15-20% on each treatment until it reached 750 mJ/cm$^2$. On the scalp, clearance was achieved with 8 treatments. Preservation treatment was continued once a week. The patient was delighted with the results.

In the above examples Psoriatic lesions began to resolve after 3-4 treatments and the majority of the lesions cleared within 8-10 treatments. Tanning was observed in the treated areas. The patients were evaluated monthly following phototherapy.

Use of a fiberoptic brush type phototherapy device of the type described above resulted in successful treatment of scalp psoriasis. It was easy for the operator to perform and well tolerated by the patient. Each session was less than 15 minutes.

One or more or any part thereof of the control, sensing, or other techniques described above can be implemented in computer hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The technique can also be implemented as a computer-readable storage medium, configured with a computer program, where the storage medium so configured causes a computer to operate in a specific and predefined manner to perform the functions described herein.

As used herein the terms "light," "optics," "optical," etc are to be understood to include electromagnetic radiation both within and outside of the visible spectrum, including, for example, ultraviolet radiation.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed:

1. A phototherapy apparatus for the treatment of skin disease comprising:
    A. an at least partially hollow body element;
    B. a plurality of light emitting elements enclosed within the body element; and
    C. a plurality of elongated light transmitting elements, each of said light transmitting elements having a proximal end detachably affixed to the body element in proximity to one or more of the light emitting elements, and extending to an end distal the body element;
    wherein, for each of the elongated light transmitting elements, at least a portion of light incident from the light emitting elements onto the proximal end is directed through the light transmitting element and emitted from the distal end and further comprising:
    D. a support element adapted to be detachably received by the body element and to support the elongated light transmitting elements;
    wherein each of the elongated light transmitting elements extends from its proximal end, to and through the support element from a side of the support element proximal the body element, to and beyond a side of the support element distal the body element, and
    E. at least one alignment element within the body element and adapted to receive the proximal end of an associated one of the elongated light transmitting elements and to maintain said proximal end in a desired position relative to an associated one of the light emitting elements,
    wherein the alignment element defines an interior region having a sidewall diverging from an end closest to the light emitting element, wherein the proximal end of the associated light transmitting element is disposed within the interior region.

2. The apparatus of claim 1, wherein the plurality of light emitting elements include at least one from the group of: a light emitting diode, a quantum dot, a solid state laser.

3. The apparatus of claim 1, wherein the plurality of light emitting elements have a spectral output within the range of 280 nm to 320 nm.

4. The apparatus of claim 3, wherein the plurality of light emitting elements have a spectral output within the range of 310 nm to 320 nm.

5. The apparatus of claim 1, wherein the plurality of light emitting elements have a spectral output within the range of 320 nm to 380 nm.

6. The apparatus of claim 1, wherein one or more of the elongated light transmitting elements comprises an optical fiber.

7. The apparatus of claim 1, wherein one or more of the elongated light transmitting elements comprises a hollow tube, the interior surface of said tube having a reflective coating.

8. The apparatus of claim 1, wherein the elongated light transmitting elements are arranged in a regular array.

9. The apparatus of claim 8, wherein the array is a two dimensional array.

10. The apparatus of claim 8, wherein the array is arranged to provide substantially uniform fluence of light emitted from the distal ends of the elongated light transmitting elements at an area of a treatment surface.

11. The apparatus of claim 1, wherein the distal end of one or more of the light transmitting elements comprises a bulbous tip comprised of a light emitting spherical segment.

12. The apparatus of claim 11, wherein the spherical segment has a radius of curvature within the range of about 0.25 mm to about 3.0 mm.

13. The apparatus of claim 1 wherein the distal end of one or more of the light transmitting elements comprises a rounded tip.

14. The apparatus of claim 11, wherein the rounded tip has a radius of curvature within the range of about 0.25 mm to about 3.0 mm.

15. The apparatus of claim 6, wherein the fiber comprises a inner core surrounded by an outer cladding, said inner core having a radius within the range of about 0.1 mm to about 3 mm.

16. The apparatus of claim 1, further comprising a sensor adapted to sense the proximity or contact of the distal end of one or more of the elongated light transmitting elements to a treatment surface.

17. The apparatus of claim 1, wherein a proximal end of at least one of the elongated transmitting elements comprises a retractable cover element, said retractable cover element adapted to cover at least a portion of said proximal end when said proximal end is detached from the body element and to retract from said proximal end when the proximal end is affixed to the body element in proximity to one or more of the light emitting elements.

18. The apparatus of claim 1, wherein at least one of the light emitting elements comprises a retractable cover element, said retractable cover element adapted to cover at least a portion of the least one light emitting when a proximal end of at least one light transmitting element is detached from the body element, and to retract from the at least one light emitting element when said proximal end is affixed to the body element in proximity to the at least one light emitting element.

19. The apparatus of claim 1, further comprising a control unit in communication with the light emitting elements configured to selectively adjust the duration or intensity of light transmitted from the light emitting elements to the light transmitting elements.

20. The apparatus of claim 19, wherein the control unit is in communication with a power supply, and is configured to control the power supplied to the light emitting elements to adjust the duration or intensity of light transmitted from the light emitting elements to the light transmitting elements.

21. The apparatus of claim 19, wherein the control unit comprises a timer.

22. The apparatus of claim 19, further comprising a dosimetry sensor adapted to, during operation, provide information to the control unit indicative of a dose of treatment light directed from the light transmitting elements to a treatment surface.

23. The apparatus of claim 22, wherein the control unit is configured to selectively adjust the duration and intensity of light transmitted from the light emitting elements to the light transmitting elements based on said information.

24. The apparatus of claim 20 further comprising the power supply, wherein the power supply is enclosed within the body element.

25. The apparatus of claim 1, wherein the body element is substantially opaque to light emitted by the light emitting elements.

26. A treatment system comprising:
    a plurality of phototherapy devices adapted to provide treatment light to a treatment area, each device comprising:
        an at least partially hollow body element;
        a plurality of light emitting elements enclosed within the body element; and
        a plurality of elongated light transmitting elements, each of said light transmitting elements having a proximal end detachably affixed to the body element in proximity to one or more of the light emitting elements, and extending to an end distal the body element;
    wherein, for each of the elongated light transmitting elements, at least a portion of light incident from the light emitting elements onto the proximal end is directed through the light transmitting element and emitted from the distal end;
    a support element adapted to be detachably received by the body element and to support the elongated light transmitting elements;
    wherein each of the elongated light transmitting elements extends from its proximal end, to and through the support element from a side of the support element proximal the body element, to and beyond a side of the support element distal the body element,
    at least one alignment element within the body element and adapted to receive the proximal end of an associated one of the elongated light transmitting elements and to maintain said proximal end in a desired position relative to an associated one of the light emitting elements,
    wherein the alignment element defines an interior region having a sidewall diverging from an end closest to the light emitting element, wherein the proximal end of the associated light transmitting element is disposed within the interior region,
    and
    a control unit adapted to selectively supply power to each of the plurality of the phototherapy devices.

27. The system of claim 26, wherein the control unit is capable of simultaneously supplying power to at least two of the plurality of phototherapy devices.

28. The system of claim 26, wherein the plurality of the phototherapy devices comprises at least two phototherapy devices each adapted to provide treatment light at a different spectral range than the other.

29. A method of treating an area of skin affected by skin disease comprising
    providing treatment light to the affected area from a phototherapy device, said phototherapy device comprising:
    A. an at least partially hollow body element;
    B. a plurality of light emitting elements enclosed within the body element; and
    C. a plurality of elongated light transmitting elements, each of said light transmitting elements having a proximal end detachably affixed to the body element in proximity to one or more of the light emitting elements, and extending to an end distal the body element;
    wherein, for each of the elongated light transmitting elements, at least a portion of light incident from the light emitting elements on the proximal end is directed through the light transmitting element and emitted from the distal end and further comprising:

D. a support element adapted to be detachably received by the body element and to support the elongated light transmitting elements;

wherein each of the elongated light transmitting elements extends from its proximla end, to and through the support element from a side of the support element proximal the body element, to and beyond a side of the support element distal the body element, and E. at least one alignment element within the body element and adapted to receive the proximal end of an associated one of the elongated light transmitting elements and to maintain said proximal end in a desired position relative to an associated one of the light emitting elements, wherein the alignment element defines an interior region having a sidewall diverging from an end closest to the light emitting element, wherein the proximal end of the associated light transmitting element is disposed within the interior region.

30. The method of claim 29, wherein providing treatment light comprises bringing the distal ends of the light transmitting elements into proximity or contact with the affected area.

31. The method of claim 30, wherein the providing treatment light comprises, while maintaining distal ends of the light transmitting elements into proximity or contact with the affected area, moving the distal ends across the affected area to provide at least one minimal erythema dose of treatment light to the affected area.

32. The method of claim 31, wherein at least a portion of the affected area is a hair bearing region, and moving the distal ends across the affected area comprises combing the distal ends through the hair.

\* \* \* \* \*